(12) United States Patent
Togino

(10) Patent No.: US 7,562,981 B2
(45) Date of Patent: Jul. 21, 2009

(54) BIOLOGICAL INFORMATION ACQUISITION AND PRESENTATION KIT, AND PUPILLARY DIAMETER MEASUREMENT KIT

(75) Inventor: Takayoshi Togino, Koganei (JP)

(73) Assignee: Olympus Corporation, Tokyo (JP)

( * ) Notice: Subject to any disclaimer, the term of this patent is extended or adjusted under 35 U.S.C. 154(b) by 111 days.

(21) Appl. No.: 11/586,450

(22) Filed: Oct. 24, 2006

(65) Prior Publication Data

US 2007/0123794 A1 May 31, 2007

(30) Foreign Application Priority Data

Oct. 25, 2005  (JP) ............................. 2005-309872
Apr. 28, 2006  (JP) ............................. 2006-126178

(51) Int. Cl.
*A61B 3/14* (2006.01)

(52) U.S. Cl. ...................................... 351/206; 351/223

(58) Field of Classification Search ................ 351/204, 351/205, 206, 211, 212, 220, 221, 222, 223, 351/239, 244; 600/300
See application file for complete search history.

(56) References Cited

U.S. PATENT DOCUMENTS

| 5,114,222 | A | * | 5/1992 | Cornsweet | .................. | 351/204 |
| 5,719,659 | A | * | 2/1998 | Suzuki | ........................ | 351/215 |
| 7,284,861 | B2 | * | 10/2007 | Fujieda | ........................ | 351/206 |
| 2006/0215112 | A1 | * | 9/2006 | Nishio et al. | ................. | 351/205 |

FOREIGN PATENT DOCUMENTS

| JP | 2002-238853 | 8/2002 |
| JP | 2004-065527 | 3/2004 |
| JP | 2004-181233 | 7/2004 |
| JP | 2004-283609 | 10/2004 |
| JP | 2005-143684 | 6/2005 |
| JP | 2005-152462 | 6/2005 |

* cited by examiner

*Primary Examiner*—Hung X Dang
*Assistant Examiner*—Tuyen Q Tra
(74) *Attorney, Agent, or Firm*—Kenyon & Kenyon LLP

(57) ABSTRACT

The invention relates to a biological information acquisition and presentation kit that enables a general able-bodied person or subject to measure the subject's own biological or emotional index in a ready way. The kit 1 is characterized by comprising a positioning means capable of being positioned on an axial focus position of a taking optical system that allows a subject to take an image of a subject's eyeball by herself or himself, an imaging means adapted to take an image of the subject's eyeball, a measurement means adapted to measure a physiological index from the image taken of the eyeball, a conversion means adapted to convert the physiological index detected by said measurement means into an emotional index, and a recording means adapted to record said physiological index or said emotional index, and further comprising a presentation means adapted to present comparative information with a recorded past emotional index.

27 Claims, 15 Drawing Sheets

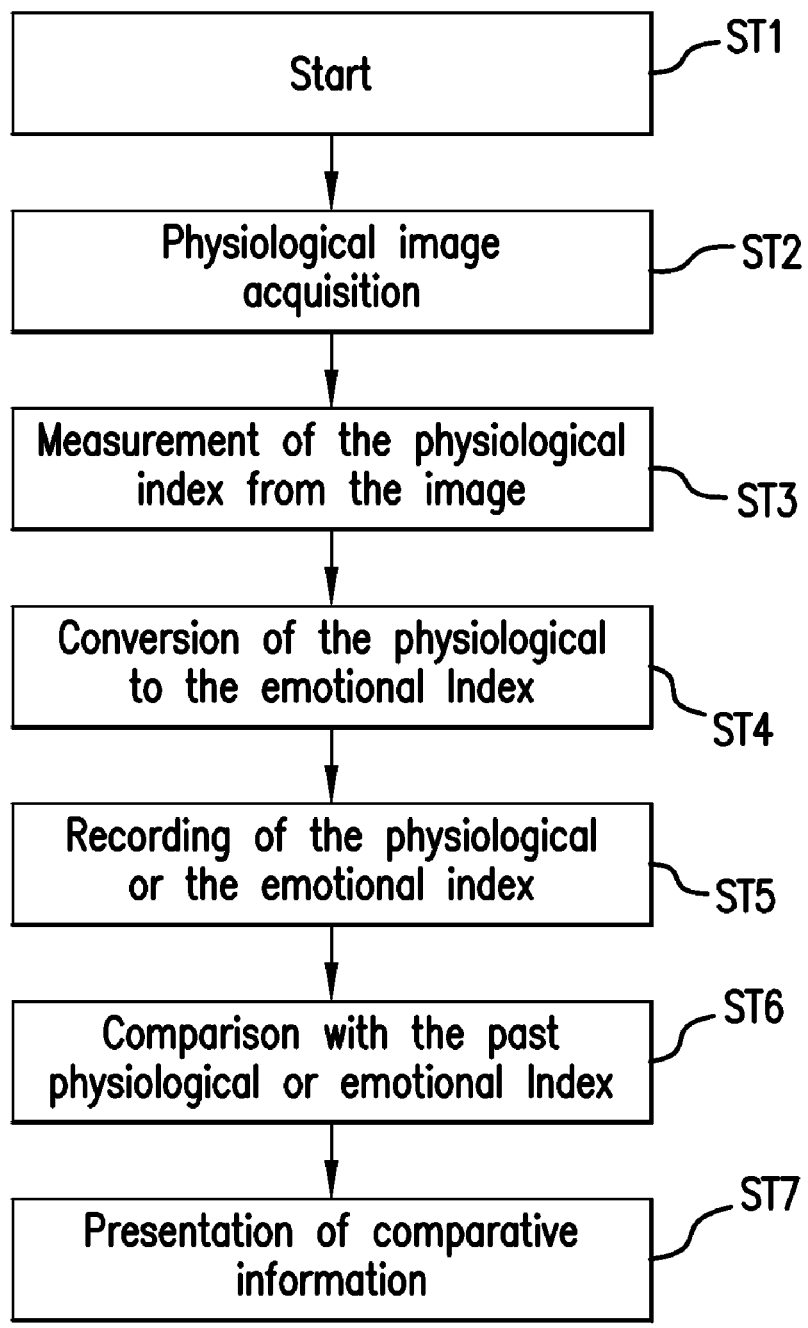

FIG.4

Pupillary light reflex and the autonomic nervous system

| Pupil size (A1) | L | %−A | %−VC$_{max}$ | %−VD$_{max}$ | VC/VD ratio | State of the autonomic nervous system |
|---|---|---|---|---|---|---|
| Pupil contraction (↓↓) | ↑ | ↓ |  | ↑ | ↓ | Exacerbation of the parasympathetic nerve |
| Pupil contraction (↓↓) | ↑ | ↑ | ↑↑ | ↑ | ↑↑ | Suppression of the sympathetic nerve |
| Dilation of the pupil (↑↑) | ↑ | ↓↓ | ↑ | ↑↑ | ↓ | Suppression of the parasympathetic nerve |
| Dilation of the pupil (↑↑) | ↑ | ↓ | ↓ | ↑↑ | ↓ | Exacerbation of the sympathetic nerve |
| Normal (→) | ↑↑ | ↓ | ↑↑ | ↑↑ | ↑ | A P D |

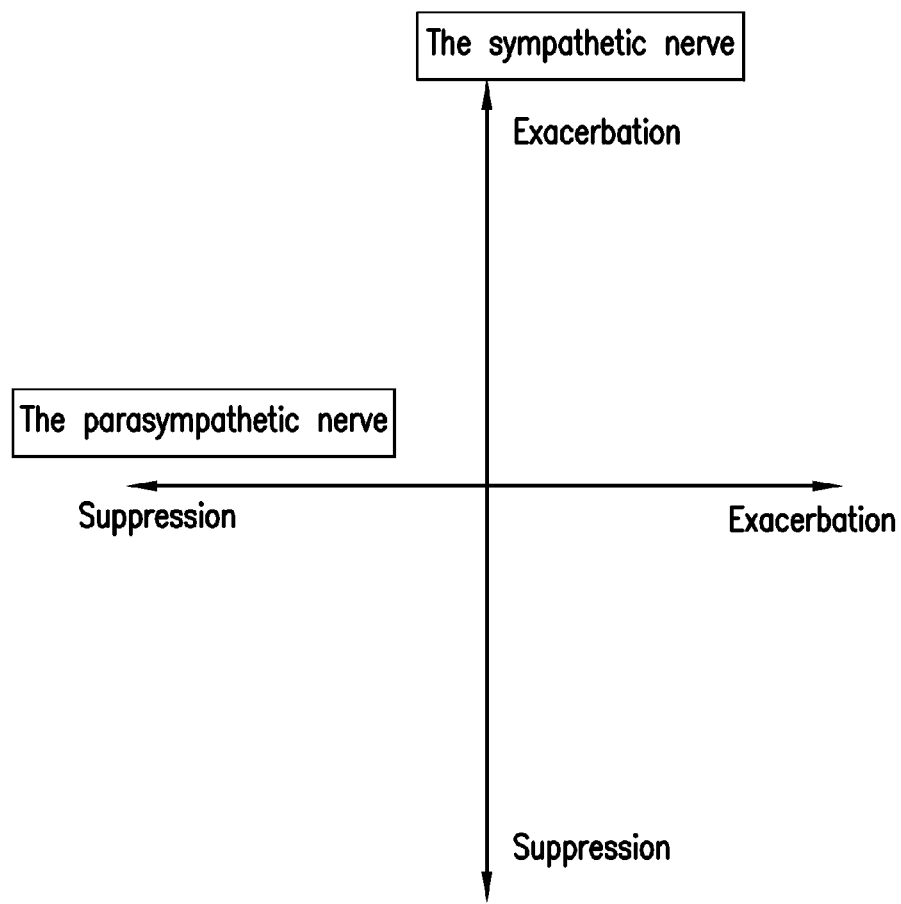

BIOLOGICAL INFORMATION ACQUISITION AND PRESENTATION KIT, AND PUPILLARY DIAMETER MEASUREMENT KIT

This application claims benefit of Japanese Application No. 2005-309872 filed in Japan on Oct. 25, 2005 and No. 2006-126178 filed in Japan on Apr. 28, 2006, the contents of which are incorporated herein by this reference.

BACKGROUND OF THE INVENTION

The present invention relates to a biological information acquisition and presentation kit, and more particularly to a measurement kit that can be used by general subjects without difficulty to manage mental health or measure the degree of stress.

Modern society is full of a lot more stressors, and people of today live their life while exposed to the repeated buildup and relief of stresses from such stressors. If you are in yourself vulnerable to stresses or cannot get rid of them, you will be in poor shape or, in the worst case, suffer from depressions. In recent years, many people have had troubles stemming from stresses, and there have been a number of methods or sites to measure stress objectively.

For instance, there are questionnaires such as CMI (the Cornel medical index for checking physical and mental health in general), TMI (for checking vegetative neurosis), SCL (the stress check list), STCL (for checking stress tolerances), Y-G personality test (the Yatabe and Gilford Personality Test), INV (the Seiken Type Personal Inventory), MAS (for checking the degree of uncertainty and fear), MMPI (Minnesota Multiphasic personality inventory), Egogram (for checking the state of ego), SDS (self-depression scale), and motivation scores (for checking the degree to which motivation is deprived).

However, these objective estimation methods are largely elusive in terms of how each one individual feels. There are further problems; for instance, too many questions take too much time to fill in, and day-to-day filling-in results in poor reliability from familiarity.

If you can estimate the degree of such psychological stress objectively and quantitatively, then you will be able to learn the degree to which you are tired, introduce suitable means for getting rid of stress in daily life, or take aggressive action for relaxation, thereby effectively maintaining and promoting day-to-day health. Further, recent studies of psychoneuroimmunology, etc. have revealed that autonomic balances due to stress are helpful for immune mechanism adjustments and have an increased risk of heat ailments and cerebral ischemia, and the optimization of autonomic balances by stress control has been expected to become preventive medicine for heart diseases, cerebrovascular accidents (cerebral hemorrhage and cerebral infarction) and cancers.

There is a method for measuring a stress marker (protein) as the objective degree of stress, for instance, a kit for measuring the degree of stress from the concentration of cortisol, etc. in saliva. However, problems with this measuring kit are that it is hard for general subjects to use and costs much for running, so it is not still put to practical use.

There are internal organs under control by both the sympathetic and parasympathetic nerves of the autonomic nervous system, among which it is the heart and an eyeball that can be measured for movements in a relatively easy yet non-invasive way.

For the heart, heart rate variation analysis for determining the degree of stress from a heart rate variation is well known in the art. For the heart rate variation analysis, there are some measuring means such as electrocardiograms and pulsimeter, and volumetric pulse waves in particular may be easily measured by the mere attachment of a photoelectric sensor clip to an earlobe. Because of the need of brining an electrode or infrared sensor into contact with the subject, however, it is unreasonable for general subjects to obtain stable measurements. Heart rates vary largely depending on attitudes and movements, and addition to the cardiovascular system of loads such as running or going up stairs are significantly reflected on them. In addition, the heart rates are sensitive to the so-called physical stress; for psychological stress measurement, it is required to rely on some limitations so as to eliminate such influences. In short, the heart rates are too difficult to measure.

On the other hand, eyeball movement in general, and a pupillary diameter in particular is directly governed by both the sympathetic and parasympathetic nerves of the autonomic nervous system in a region surround by the sphincter muscle of pupil having a centripetal path starting from the retinal optic nerve and a centrifugal path governed primarily by the autonomic nerve plus the parasympathetic nerve and the dilator pupillae muscle governed by the sympathetic nerve; the eyeball is the only one organ whose movement can be measured in a non-contact way. Further, the dilator pupillae muscle and the sphincter muscle of pupil are governed by the sympathetic and parasympathetic nerves with no neurotransmitter interleaved between them, and so they have a feature of being fast responsive.

In this regard, some methods of measuring a pupillary diameter have been known from Patent Publications 1 to 4. With such measuring methods wherein a measurer brings a measuring kit in alignment with the pupillary position of a subject, however, it is not possible for the subject to bring the measuring kit in alignment with the subject's own pupil for measurement.

Patent Publication 4 shows a measuring kit wherein a fixed lamp is presented to one eyeball of a subject while an infrared illuminator and an infrared camera are positioned relative to another eyeball of the subject to take an image of the pupil, and a visible light photo-stimulus is presented to measure the then pupillary light reflex, thereby working out various parameters for pupillary light reflex. Because the attachment of the kit to the subject keeps the subject perfectly out of sight, the subject is forcibly placed in tension, or measurement cannot be carried out unless the subject is sitting on a chair or lying down on bed.

Patent Publication 5 shows how to detect where in a visual field the focus of the eye is set, and says nothing about conversion into a physiological or emotional index.

Patent Publication 6 shows equipment for letting a physician measure the pupillary light reflex of a patient; that is, it is not possible for general subjects to achieve alignment by themselves.

Patent publication 7 shows equipment that is adapted to primarily feed a respiration rate back to a user, and which may also detect partial nictitation (wink). With this equipment, however, it is not possible to measure the rotary motion of an eyeball or a pupillary diameter.

Patent Publication 1
JP(A) 2002-238853
Patent Publication 2
JP(A) 2004-283609
Patent Publication 3
JP(A) 2004-65527
Patent Publication 4
JP(A) 2005-143684

Patent Publication 5

JP(A) 2004-181233

Patent Publication 6

JP(A) 2004-283609

Patent Publication 7

JP(A) 2005-152462

Non-Patent Publication 1

"Shingaku Giho", MBE2004-127 (2005-03), pp. 17-20 "Studies on the estimation capability of pupillary area during nictitation"

Non-Patent Publication 2

"Neurology", 42:302-314, 1995, "Pupillary Reflex"

Non-Patent Publication 3

"Clinics & Studies", Vol. 73, No. 12 (1996-12), pp. 234-145, "Electronic Pupilometer Iris Coder Seminar"

Non-Patent Publication 4

"Neuroophthalmology", Vol. 10, No. 2 (1993), pp. 131-136, "Applications of iris coders in ophthalmology"

SUMMARY OF THE INVENTION

In view of such states of the prior art as described above, one object of the present invention is to provide a biological information acquisition and presentation kit that can let an ordinary able-bodied person or subject measure her or his own biological or emotional index in a ready way.

Another object of the present invention is to provide a pupillary diameter measurement kit that can let an ordinary able-bodied person or subject measure her or his own pupilary diameter or pupillary movement in a ready way without recourse to someone else, and in an objective way with high accuracy.

To accomplish the above objects, the present invention provides a biological information acquisition and presentation kit, characterized by comprising a positioning means capable of being positioned on an axial focus position of a taking optical system that allows a subject to take an image of a subject's eyeball by herself or himself, an imaging means adapted to take an image of the subject's eyeball, a measurement means adapted to measure a physiological index from the image taken of the eyeball, a conversion means adapted to convert the physiological index detected by said measurement means into an emotional index, and a recording means adapted to record said physiological index or said emotional index, and further comprising a presentation means adapted to present comparative information with a recorded past emotional index.

The present invention also provides a biological information acquisition and presentation kit, characterized by comprising a search and track means adapted to search out and track a subject's eyeball, an imaging means adapted to take an image of the subject's eyeball, a measurement means adapted to measure a physiological index from the image taken of the eyeball, a conversion means adapted to convert the physiological index detected by said measurement means into an emotional index, and a recording means adapted to record said physiological index or said emotional index, and further comprising a presentation means adapted to present comparative information with a recorded past emotional index.

Preferably, said positioning means comprises an optical system having positive power, which is adapted to enlarge a subject's pupil, permitting the subject to observe an enlarged subject's pupil.

Preferably, said physiological index is a rotary motion of the eyeball, nictitation, or a pupillary diameter.

Preferably, said imaging means comprises an infrared illumination means, and imaging is implemented by infrared radiation.

Preferably, said imaging means comprises a photo-stimulating means adapted to bring on a visible light photostimulus.

Preferably, the biological information acquisition and presentation kit further an identifying function capable of specifying who is the subject.

Preferably, said emotional index is a one-dimensional variable indicative of antagonistic activation of a sympathetic nerve and a parasympathetic nerve of the autonomic nervous system, or a two-dimensional variable indicative of antagonistic activation of a sympathetic nerve and a parasympathetic nerve of the autonomic nervous system, respectively.

Preferably, the biological information acquisition and presentation kit further comprises a clock adapted to record measuring time along with said physiological index or said emotional index.

Preferably, the biological information acquisition and presentation kit further has a day, week, month or year-base variation analysis mode capable of checking up the periodicity of said physiological index or said emotional index.

Preferably, said measurement means uses FFT or wavelet transformation.

Preferably, the biological information acquisition and presentation kit is to be attached to a compact or a dressing table or, alternatively, it may be either of a cellular phone type or of a toy type.

Further, the present invention provides a pupillary diameter measurement kit that allows a subject to measure a subject's own pupillary diameter, characterized by comprising a reflecting surface having at least a reflection function of enabling the subject to observe an image of the subject's own pupil, an alignment mark adapted to align the subject's pupil, an infrared imaging device located in opposition to the subject's pupil with said reflecting surface interposed therebetween, an infrared illumination means adapted to illuminate the subject's pupil, a projection optical system adapted to project an image of the subject's pupil onto an imaging plane of said infrared imaging device, and an analysis means adapted to compute and analyze pupillary size on the basis of pupillary image information sent out of said infrared imaging device.

Preferably, the pupillary diameter measurement kit further comprises an optical system having positive power, which has a function of projecting the subject's pupil as an enlarged virtual image in front of the subject's pupil.

Preferably, said optical system having positive power comprises a positive lens or a positive Fresnel lens or, alternatively, it comprises a concave mirror or a Fresnel concave mirror.

For said reflecting surface having a reflecting function, for instance, a semi-transmitting mirror or a holed mirror may be used.

Alternatively for said reflecting surface having a reflecting function, for instance, a plane mirror or a concave mirror may be used.

Preferably, said infrared illumination means comprises a sheet polarizer adapted to turn illumination light into linearly polarized light, and said projection optical system is provided with another sheet polarizer that transmits linearly polarized light in a direction orthogonal to the first-mentioned sheet polarizer.

Preferably, the pupillary diameter measurement kit further comprises a surface having a second reflecting function of projecting the alignment mark in front of the subject's pupil.

With the inventive biological information acquisition and presentation kit, it is possible to measure a general subject's own present physiological index and learn the degree to which the present emotional index varies from the biological or emotional index estimated from the result of measurement of the past biological information, thereby obtaining feedbacks with which the subject can figure out an appropriate balance between stress and relaxation or get an opportunity of tackling with improvements in life quality.

With the inventive pupillary diameter measurement kit, for instance, it is possible for an ordinary able-bodied person or subject to estimate the degree of stress or relaxation in a ready, objective way with high accuracy yet without recourse to someone else.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

BRIEF DESCRIPTION OF THE DRAWINGS

FIG. 3 is a block diagram for the whole processing with the inventive physiological information acquisition and presentation kit.

FIG. 4 is illustrative of a physiological index vs. emotional index relation used for the conversion of a physiological index to an emotional index.

FIG. 5 is a one-dimensional graph illustrative of antagonistic activation of the sympathetic and parasympathetic nerves of the autonomic nervous system.

FIG. 6 is a two-dimensional graph illustrative of activation of the sympathetic and parasympathetic nerves of the autonomic nervous system, respectively.

DESCRIPTION OF THE PREFERRED EMBODIMENTS

The physiological information acquisition and presentation kit and pupillary diameter measurement kit according to the present invention are now explained specifically with reference to some examples.

Figure 1:
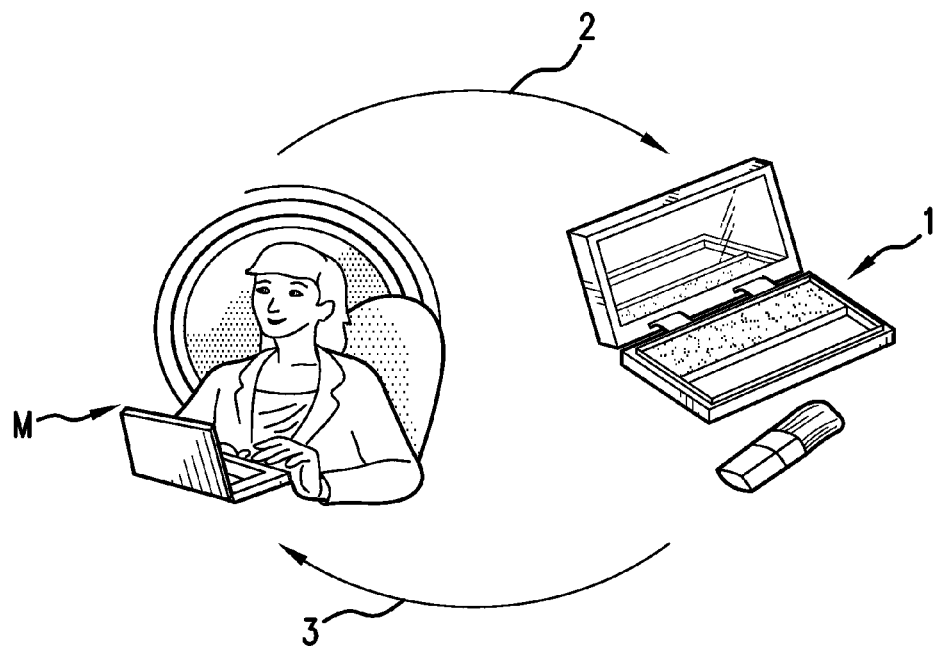
FIG. 1 is illustrative in conception of the physiological information acquisition and presentation kit.

FIG. 1 is illustrative in conception of the physiological information acquisition and presentation kit according to the present invention. The inventive physiological information acquisition and presentation kit 1 is, in a manner of speaking, a mental weighing machine. Although a weighing machine is used for weighing after day-to-day bathing as an example, yet it does not form any judgment of whether there is normality or abnormality. Weight control is left to the subject herself or himself; the subject makes a rule of controlling weight while taking lack of exercise and diet calories into account. If you can learn your weight in terms of number, you will control yourself with some self-potency and a feeling of achievement and, at the same time, you will be able to figure out the next target with a lot more satisfaction or positive feedbacks. Similarly, the physiological acquisition and presentation kit 1 of the present invention, too, can visualize or objectify your mental state in terms of number, so that you can control yourself, keeping your best state going on through self-potency.

To this end, it is required to have a specific kit at the ready, which can be easily operated by anybody with no difficulty and enables a mental state to be objectively measured with no need of any hard-to-understand knowledge. With equipment used so far for pathological examination and diagnosis, there is a problem that an expert must inspect an unspecified large number of subjects with much time and precision.

The physiological acquisition and presentation kit 1 of the present invention is now explained with reference to FIG. 1. The present invention is applied to each one or several subjects. For instance, you (subject M) may use the inventive physiological acquisition and presentation kit 1 to measure (2) the physiological or emotional index at the time of getting up. If you learn that your vital power grows low today as compared with the results of measurement the day before, a weak earlier or the like, you will be able to change your behavior that day or leave off work a little earlier, going home for rewinding. Conversely, if your vital power grows high, you will be able to work overtime until late, getting job done. Thus, you (subject M) will able to take action (3) by yourself to improve on the physiological or emotional index according to what is measured by, and presented on, the inventive physiological acquisition and presentation kit 1. The inventive physiological information acquisition and presentation kit 1 is bound to be used to set off changes in the behavior of the subject M according to what is presented on it. You would like to keep your mental state from someone else. With equipment that cannot take measurements unattended, for instance, it is impossible to take measurements every morning.

According to the present invention, the kit 1 is characterized by comprising a positioning means that enables the subject M to bring her or his own eyeball in alignment with an imaging optical system. The positioning means could just as easily be a cylindrical mechanical positioning means 11 as shown typically in FIG. 2. With the positioning means 11 of the inventive physiological information acquisition and presentation kit 1 in light engagement with the eye, it is possible to bring the eyeball on a focus point on an optical axis within the kit 1.

FIG. 3 is a block diagram for the whole processing by the inventive physiological information acquisition and presentation kit 1.

Step ST1: Start

Eyeball image acquisition may be kicked off by use of a start button, or acquiring an image of contrast after power is put on.

Step ST2: Physiological Information Acquisition

The physiological information acquisition and presentation kit 1 comprises an imaging means made up of a taking optical system adapted to acquire an image of the subject's eyeball and an imaging device, and that imaging means is used to take a pupillary diameter measurement for several tens seconds to acquire an image. Preferably, the taken image is processed as set forth typically in Non-Patent Publication 1 to estimate a pupillary diameter at the time of nictitation. It is more preferable to measure a pupillary diameter change due to reflex from a flash or stimulating light or noise.

Referring briefly to the processing of Non-Patent Publication 1, that processing involves an estimative interpolation by Support Vector Regression of a pupillary area at the time of nictitation from time-series data about a pupillary area inclusive of nictitation.

Step ST3: Measurement of Physiological Index from the Image

The physiological information acquisition and presentation kit 1 comprises a measuring means adapted to measure the physiological index from the acquired certain-time eyeball image, wherein the physiological index includes changes in nictitation interval, movement of the line of sight, pupillary diameter and so on. It is more preferable to give visible stimulating light to the eyeball as a stimulant, thereby working out various parameters set forth Non-Patent Publications 2, 3 and 4 from the then pupil variations. Preferable parameters, for instance, are pupillary area before stimulation (A1), latency (L), pupil contraction quantity (A3), maximum pupil contraction speed ($VC_{max}$), and maximum pupil dilation speed ($VD_{max}$). These parameters are explained in Non-Patent Publications 2, 3 and 4.

Step ST4: Physiological-to-Emotional Index Conversion

The physiological index acquired at Step ST3 is converted into the emotional index. That conversion, for instance, is implemented by numerical processing based on Table 1 (FIG. 4) at page 133 of Non-Patent Publication 4. What is here important is to learn changes in the numerical value, not the numerical value itself; the purport of the present invention is not to form a judgment of whether there is normality or abnormality. For the meanings of the symbols in FIG. 4, see Non-Patent Publication 4.

Step ST5: Recording of the Physiological or Emotional Index

The physiological index acquired at Step ST3, and the emotional index acquired at Step ST4 is recorded in a memory or memory medium affixed to the kit.

Step ST6: Comparison with the Past Physiological or Emotional Index

The present index is offered for comparison with, or simultaneously with, the past one to learn your (subject M) recent tendencies. As a result, you can figure out the target which you will be able to try to attain with power, say, self-potency, so that you can live your life while taking your metal environment into account.

Step ST 7: Presentation of Comparative Information

Changes in the physiological or emotional index are presented to the subject with such a graph as in FIG. 5, such a two-dimensional scatter diagram as in FIG. 6, a face mark indicative of human feelings, etc. To this end, a two-dimensional display or voice may be used.

Next, specific examples of the inventive physiological information acquisition and presentation kit and the inventive pupillary diameter measurement kit are described.

EXAMPLE 1

Figure 2:
FIG. 2 is illustrative of the physiological information acquisition and presentation kit according to Example 1 of the present invention, which comprises a mechanical positioning means.

FIG. 2 is illustrative of the physiological information acquisition and presentation kit 1. A positioning means 11 is built up of a mechanical cylindrical member that should preferably be of light block capability or semi-transparency so as to be less likely to be affected by ambient light.

More preferably, that cylindrical positioning means 11 should be semi-transparent, because ambient light enters it to minimize a brightness difference between the eyes of a measurer M to be tested and not tested, making sure measurements at a more natural pulilary diameter. It is also possible to make the positioning means 11 full opaque and, at the same time, position a light source within the cylindrical positioning means 11.

If the focus of a taking optical system remains in alignment with near the end of the cylindrical member of the positioning means 11 (that engages the eye to be tested), it is possible to dispense with any focusing mechanism. Although not shown, the physiological information acquisition and presentation kit 1 includes in it an imaging device sensitive to infrared radiation, an illumination light source for infrared radiation and a light emitter for giving photostimuli to the subject's eye to be tested by way of visible light.

Figure 7A:
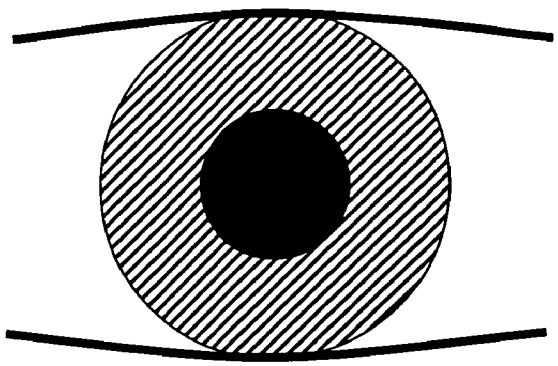
FIG. 7 is illustrative of an eyeball image taken under off-axis illumination and its reflected light quantity distribution.
Figure 7B:
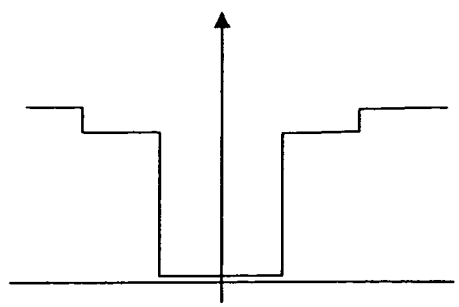

Reference is then made to the means for measuring the area or the horizontal diameter of the pupil from an image taken of the pupil of the subject M. When the eyeball is illustrated off-axially or obliquely, the light reflected off the pupil is picked up; however, the light reflected off the eyeground is not picked up through the pupil so that the pupil looks black (FIG. 7(a)). Note here that FIG. 7(a) shows a pupilary image taken with off-axis illumination, and FIG. 7(b) is indicative of the then reflected light quantity distribution. Therefore, if the reflected light quantity distribution is vinarized with any threshold, it is then possible to measure a pupilary area by counting the number of pixels in a black site corresponding to the pupil. For horizontal diameter measurement, it is only needed to find a maximum diameter by implementing the above processing in the horizontal direction. The pupil is not always in a perfect circle shape, so the area should preferably be found, but the light resulting from the reflection of illumination light at a corneal surface, an eyelid and eyelashes are likely to be carried over as noise to the found area. In general able-bodied people applications for which the inventive physiological information acquisition and presentation kit 1 is intended, it is more preferable to rely on the method of finding the horizontal diameter.

Figure 8A:
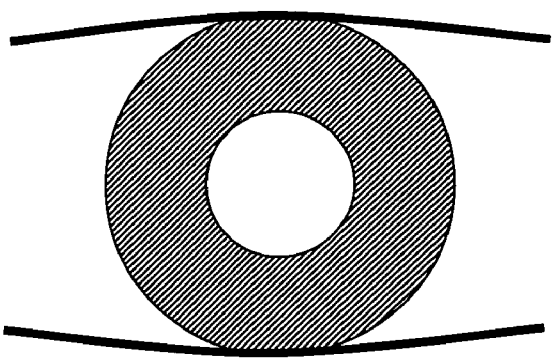
FIG. 8 is similar to FIG. 7 in the event of coaxial illustration.
Figure 8B:
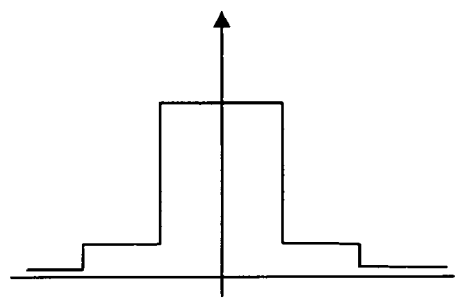

When the illumination light is coaxially incident, reflection from the eyeground grows tight, so the pupil looks white as depicted in FIG. 8(a). Note here that FIG. 8 is similar to FIG. 7 for coaxial illumination. In this case, too, the reflected light quantity distribution (FIG. 8(b)) may be binarized with any threshold to measure the size of the pupil.

More preferably, the above two modes (off-axis illumination and coaxial illumination) should be run in a fast changeover fashion to take differential images, so that the size of the pupil can be measured with no or little noise.

Figure 9A:
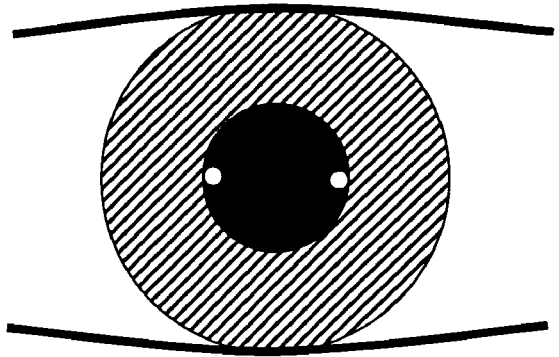
FIG. 9 is illustrative of the first Purkinje image at the time when infrared illumination light is incident on it from the horizontal, and the vertical direction.
Figure 9B:
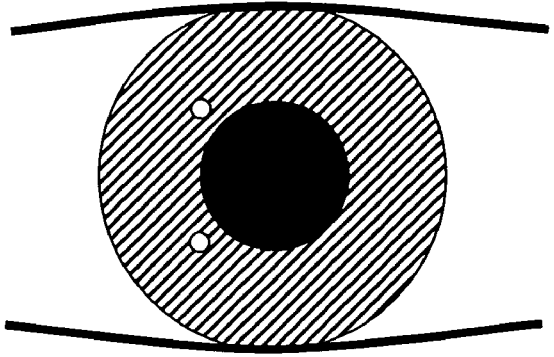

More preferably, the eyeball should be illuminated with infrared light from a direction orthogonal to the direction of measuring the pupillary diameter. As infrared illumination light strikes upon the eyeball from the horizontal direction as depicted in FIG. 9(a), it causes the first Purkinje image (corneal surface reflection) to leave in the horizontal direction. In turn, it becomes noise at the time when the pupillary diameter in the horizontal direction is measured, resulting in inability to take precise measurements. When the pupillary diameter is measured in the horizontal direction, therefore, it is desired that illumination be implemented from the vertical direction, as depicted in FIG. 9(b). More preferably, the optical axis of illumination should have a tilt of 45° or greater to the optical axis of observation so as to keep the Purkinje image from entering the pupil as much as possible.

It is desired that on the upper surface of the physiological information acquisition and presentation kit 1, there be a display unit mounted for presenting measurement data of the subject M together with the past measurement data for comparison purposes.

More desirously, an infrared illumination light source and a visible light cut filter for cutting off visible light should be used to take an image of the eyeball with infrared radiation, thereby reducing influences of taking light.

EXAMPLE 2

Figure 10:
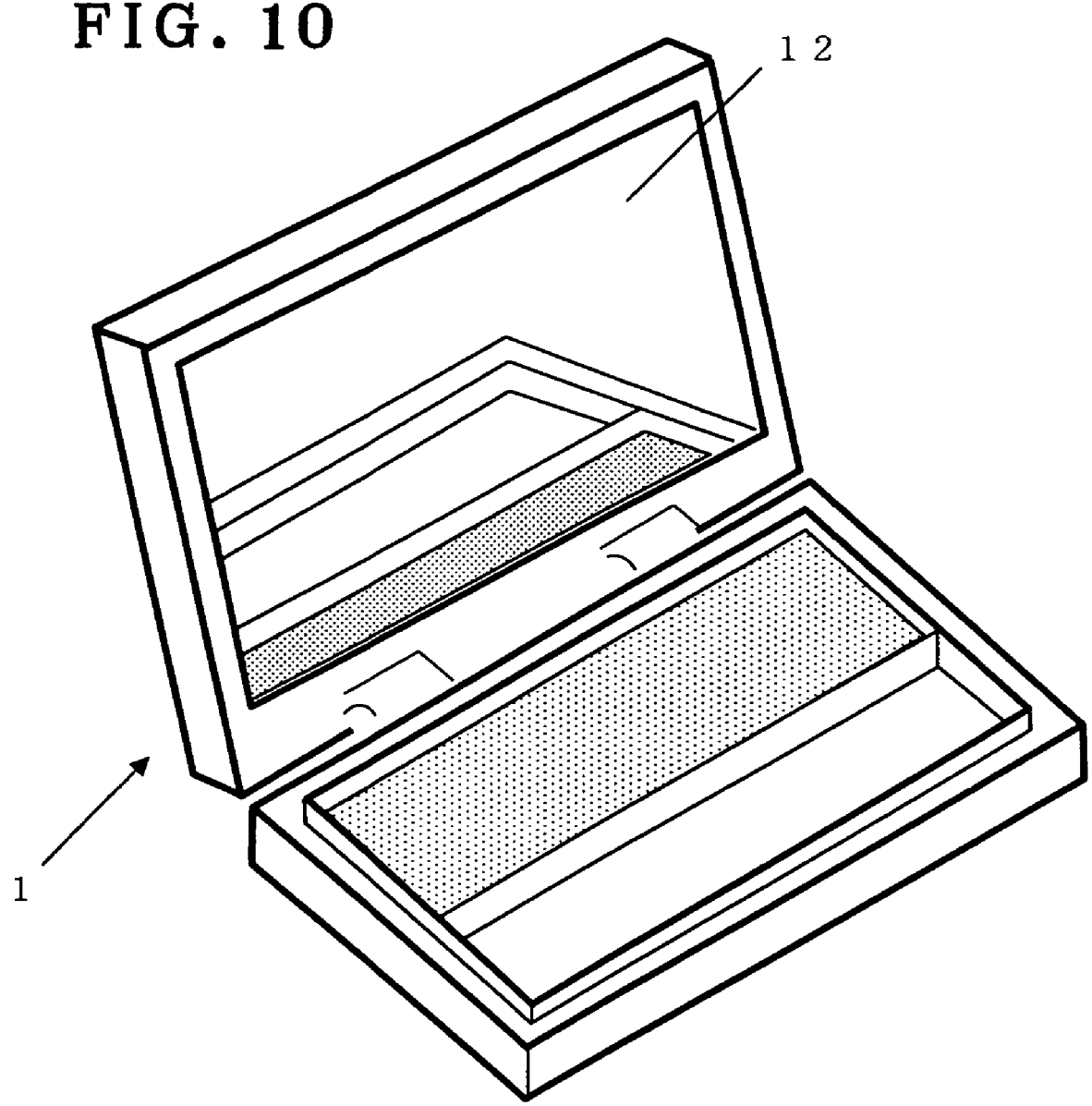
FIG. 10 is illustrative of the physiological information acquisition and presentation kit according to Example 2 of the present invention.

FIG. 10 is illustrative of the physiological information acquisition and presentation kit 1 according to Example 2. The example here is directed to a compact biological information acquisition and presentation kit that comprises an optical positioning means as the positioning one. Making measurement under perfectly non-contact conditions possible, that optical positioning means is intended for females in particular, because the measurement can be implemented with makeup intact. The kit 1 may also be used as an ordinary compact; a taking unit (an image-formation optical system, an image device, etc.) is incorporated behind a compact mirror 2 so that the subject can take an image of her own eyeball while putting on makeup or the like.

The optical positioning means in the example here comprises an imaging optical system and an imaging device in opposition to the pupil of the subject with a reflecting surface having a reflecting function interposed between them. An imaging optical path is required to have positive power, and defined by the imaging optical system adaptive to project the pupil of the subject onto an imaging plane and the imaging device positioned at its projection plane. That positive power allows an image around the subject's pupil to be projected onto the imaging device on a reduced scale.

On the other hand, it is important for a positioning optical path to have a reflecting function. This positioning optical path is necessary for the subject M to observe her or his own pupil. As a reflecting surface to this end, the compact mirror 12 of the compact is used in the example here.

The physiological information acquisition and presentation kit 1 of the example here or the head of the subject M is adjusted such that the subject M projects her or his own pupil onto the reflecting surface 12 in the postioning optical path at the center of an alignment mark.

In this state where the pupil of the subject M is projected onto the surface of the imaging device, as a measurement start button is pressed down, pupillary diameter measurement starts up.

The optical positioning means (pupillary diameter measurement kit) is now explained with reference to FIGS. 11 to 17.

Figure 11:
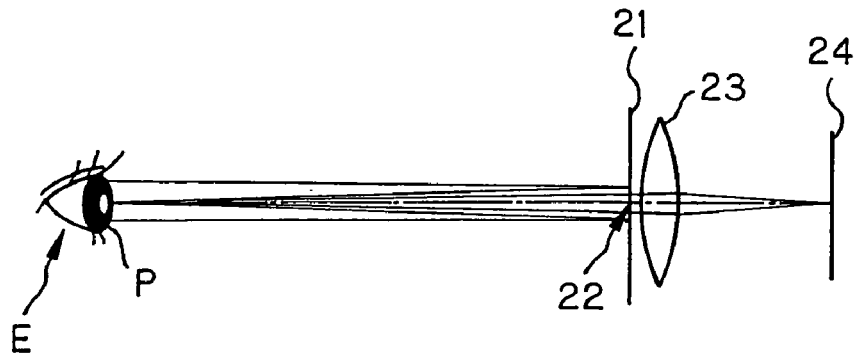
FIG. 11 is illustrative in section of an optical path for the optical positioning means according to the first embodiment of the present invention.

FIG. 11 is illustrative in section of an optical path taken by the optical positioning means according to the first embodiment of the present invention. On the entrance side of an image-formation optical system 23 for taking an image of the pupil P of the subject's eye E, there is a plane mirror 21 (compact mirror 21) disposed, which makes it possible to observe the pupil (the iris) P of the subject's eye E by the subject's own eye E, and on the image-formation side of the image-formation optical system 23 that faces away from the plane mirror 21, there is an imaging device 24 disposed, which is to take an image of the pupil (the iris) P of the subject's eye E, so that the pupil P of the subject can be projected by the image-formation optical system 23 onto the imaging plane of the imaging device 24. The plane mirror 21 here is made up of a half-silvered mirror, a dichromatic mirror adaptive to reflect visible light but transmit infrared light or such a holed mirror as will be described later so as to form the image of the subject's pupil P through that plane onto the imaging plane of the imaging device 24. And then, an alignment mark 22 such as crosshairs is provided at the center of a position of the plane mirror 21 through which the optical axis of the image-formation optical system 23 passes, so that the subject can implement alignment while taking a look at the image of the subject's own pupil P projected onto the plane mirror 21.

With such arrangement, the optical positioning means according to the embodiment here or the head of the subject can be moved and adjusted such that the alignment mark 22 lies at the center of the image of the subject's own pupil P, while the subject takes a look at the subject's own pupil P projected onto the plane mirror 21. In this state where the pupil P of the subject's eye E is projected through the image-formation optical system 23 onto the imaging plane of the imaging device 24, as the subject puts on a measurement start button not shown, pupillary diameter measurement starts up. Note here that no detailed explanation of analysis means adaptive to record pupilary image information sent out of the imaging device 24 and calculate and analyze the size of the pupil P on the basis of that information is given because they are well known from the prior publications already noted, or the like.

With the inventive pupillary diameter taking kit, it is practically unlikely to implement measurement from at least 1 meter distances; however, the human eye can be adjusted from ∞ down to 30 cm and the position of the eye E to be tested is variable, so the inventive pupillary diameter taking kit is required to have a wide range of focal depth.

In the example here, a half-silvered mirror is used for the reflecting surface of the plane mirror 21, but of course, it is acceptable to use a dichromatic mirror having the properties of transmitting infrared light but reflecting visible light.

As mentioned above, the optical axis position of the eye E to be tested is erratic; that is, it is more preferable or important for the F-number, Fno, of the image-formation optical system 23 to satisfy condition (1) so as to make sure the taking optical system has a sufficient focal depth.

$$Fno>10 \tag{1}$$

As the lower limit of 10 is not reached, the focal depth becomes insufficient, often causing the pupil P of the subject to be out of focus and, hence, leading to inability to measure the pupillary diameter precisely.

It is more preferable to satisfy condition (2):

$$Fno/P>5 \tag{2}$$

Here P is the pixel pitch in μm of the imaging device 24. This condition is about focal depth, too. However, as the pixel pitch becomes small, the focal depth grows large, so it is desired to satisfy condition (2).

Figure 12:
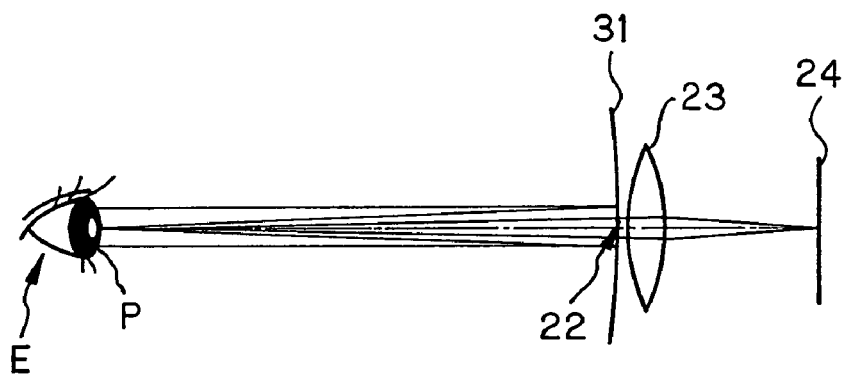
FIG. 12 is illustrative in section of an optical path for the optical positioning means according to the second embodiment of the present invention.

FIG. 12 is illustrative in section of an optical path taken by the optical positioning means according to the second embodiment. In the embodiment here, a concave mirror 31 in place of the plane mirror 21 of FIG. 11 is disposed on the entrance side of an image-formation optical system 23. The concave mirror 31 is made up of a half-silvered mirror, or a dichromatic mirror that reflects visible light and transmits infrared light. Otherwise, the second embodiment is the same as the first one. Here let f be indicative of the focal length of the concave mirror 31, and consider the case where the image of the pupil P of the subject's eye E projected from a distance longer than the focal length f onto the concave mirror 31 is observed. The observed image is upended, meaning that the eye E of the subject can be positioned shorter than the focal position of the concave mirror 31. When the eye E of the viewer is adjusted to infinity, the position of the pupil P shifts from the concave mirror 31 to the position of the focal length f. As the diopter of the subject shifts to a near point side, the position of the pupil P moves from the focal position toward the concave mirror 31 side, but that change grows small.

Otherwise, the longitudinal magnification of the concave mirror 31 is defined by a square of lateral magnification. At a position where the lateral magnification is greater than 1, therefore, the position of the image of the pupil P changes sharply in association with a change of the optical axis position of the pupil P with respect to the concave mirror 31, so the range of the position that can be taken up by the pupil P grows very narrow.

In the example here wherein the concave mirror 31 is used instead of the plane mirror 21, therefore, the position of the subject's eye E in the optical axis direction would be almost invariably fixed.

It is more preferable and important to satisfy condition (3):

$$20<f<300 \tag{3}$$

Here f is the focal length in mm of the concave mirror 31. As the lower limit of 20 mm is not reached, there is a decrease in the working distance WD of the position that can be taken up by the eye E to be tested, which would give the subject a feeling of being oppressed. As the upper limit of 300 mm is exceeded, there is a large WD change caused by a change in the diopter of the observer, which would result in an increased error of pupillary diameter measurements.

To make sure a sufficient focal depth, it is more preferable and important for the F-number, Fno, of the image-formation optical system 23 to satisfy condition (4):

$$Fno>5 \tag{4}$$

As the lower limit of 5 is not reached, the focal depth becomes insufficient, often causing the pupil P of the subject to be out of focus and, hence, leading to inability to measure the pupillary diameter precisely.

It is even more preferable to satisfy condition (5):

$$Fno/P>1 \tag{5}$$

Here P is the pixel pitch in μm of the imaging device 24. This condition is about focal depth, too. However, as the pixel pitch becomes small, the focal depth grows large, so it is desired to satisfy condition (5).

Figure 13:
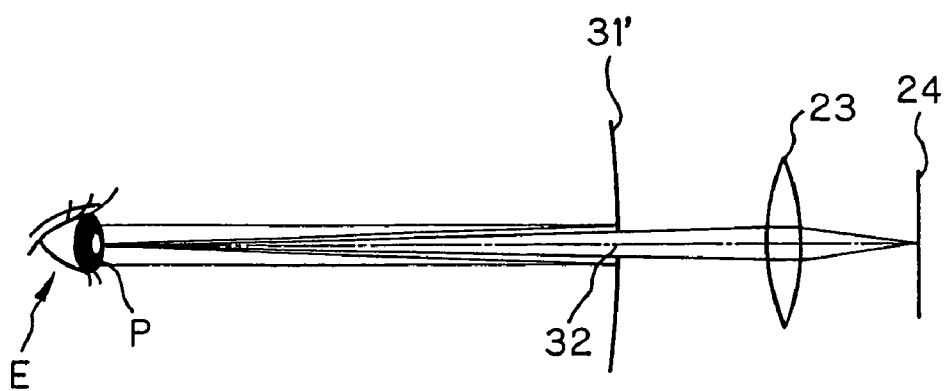
FIG. 13 is illustrative in section of an optical path for the optical positioning means according to the third embodiment of the present invention.

FIG. 13 is illustrative in section of an optical path taken by the optical positioning means according to the third embodiment, wherein a holed concave mirror 31' is used instead of the concave mirror 31 of FIG. 12, which comprises a half-silvered mirror, or a dichromatic mirror that reflects visible light and transmits infrared light. And then, a hole 32 in that concave mirror 31' is used in place of the alignment mark 22. Note here that such a hole 32 may just as easily be used in combination with an alignment mark 22 provided at the center of that hole 32. In this case, the hole 32 works as an opening for passing a light beam adapted to project the pupil P onto an imaging device 24, so the entrance pupil position of an image-formation optical system 23 is preferably disposed near the holed concave mirror 31'. Otherwise, the third embodiment is the same as the first, and the second embodiment.

For this arrangement it is preferable to satisfy condition (6):

$$E/f<1 \tag{6}$$

Here E is the distance between the holed concave mirror 31' and the entrance pupil of the image-formation optical system 23. As the upper limit of 1 is exceeded, an area around the image of the pupil P is shaded by the hole 32, or there is no sufficient light quantity obtained. As a result, the calculation and analysis of the pupillary diameter cannot be often implemented with good precision.

Figure 14:
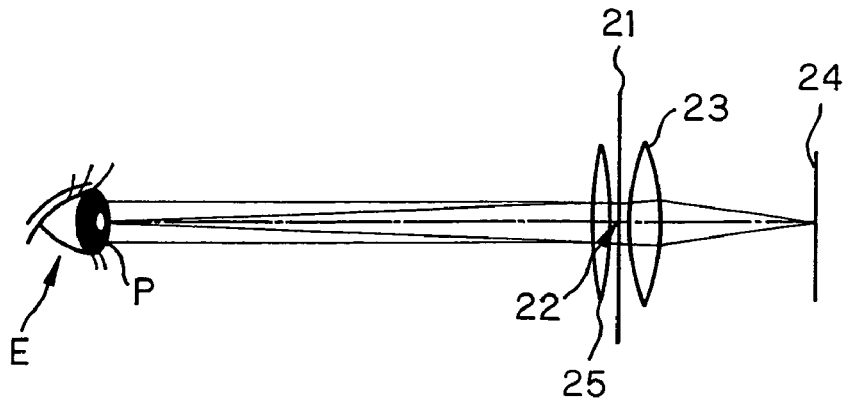
FIG. 14 is illustrative in section of an optical path for the optical positioning means according to the fourth embodiment of the present invention.

FIG. 14 is illustrative in section of an optical path taken by the optical positioning means according to the fourth embodiment, wherein a positive lens 25 is disposed in front of, and proximate to, a plane mirror 21 built up as depicted in FIG. 11 so that the positive lens 25 and the plane mirror 21 have the same function as the concave mirror 31 of FIG. 12.

In this case, a light ray adaptive to project the pupil P makes round trips through the positive lens 25, so the substantial focal length of the positive lens 25 with respect to the round-trip optical path is about half the focal length of the positive lens 25.

Figure 15:
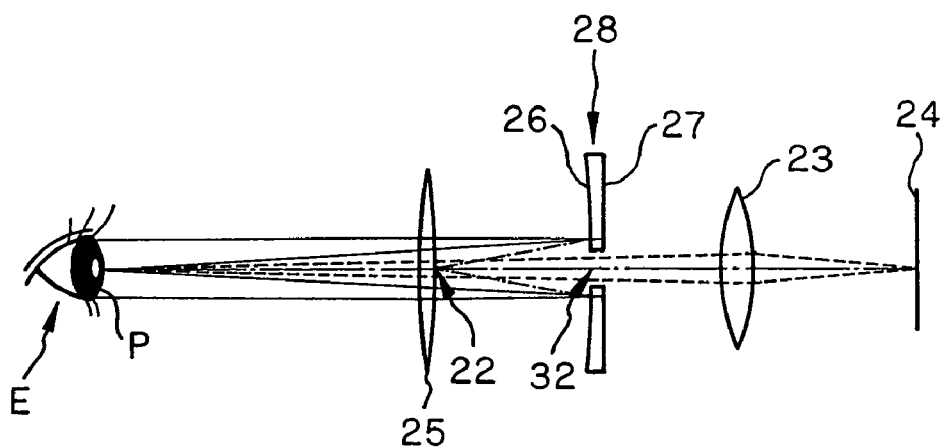
FIG. 15 is illustrative in section of an optical path for the optical positioning means according to the fifth embodiment of the present invention.

FIG. 15 is illustrative in section of an optical path taken by the optical positioning means according to the fifth embodiment, wherein there are two reflecting surfaces 26 and 27. One reflecting surface 27 is to allow the subject to view the subject's pupil P, and another reflecting surface 26 has a semi-transmitting function of projecting an alignment mark 22 provided on the back side of a double-convex positive lens 25 as a virtual image in front of the subject. The reflecting surface 27 here is made up of a plane mirror, and the reflecting mirror 26 here is made up of a concave mirror. A transparent medium with a refractive index of 1 or greater is disposed between the reflecting surfaces 26 and 27, building up a back-surface mirror 28 having negative power, the front surface of which has a semi-transmitting function.

Accordingly, the image of the pupil P of the subject is formed as a virtual image substantially at infinity by the negative-power back-surface mirror 28 by way of the double-convex positive lens 25, and to the subject's eye E, that virtual image is seen at a given distance by way of the double-convex positive lens. On the other hand, the alignment mark 22 provided on the back side of the double-convex positive lens 25 is formed as a virtual image substantially at infinity by the semi-transmitting reflecting surface 26, which image overlaps the image of the pupil P of the subject, and to the eye E of the subject, that virtual image is again seen at a given distance by way of the double-convex positive lens 25. With the arrangement of the embodiment here, therefore, the subject can adjust her or his diopter and focus to the image of the alignment mark 22 shown in the distance. And then, in that state, the subject can move her or his own eye E back and forth to bring the axial direction position of the eye E in alignment with the image of that alignment mark 22. Thus, the adjustment of the position and diopter of the eye E of the subject is so unequivocally determined that there can be no or little pupillary diameter variation from position to position.

To make sure a sufficient focal depth, it is more preferable and important for the F-number, Fno, of the image-formation optical system 23 to satisfy condition (7):

$$Fno > 1.8 \quad (7)$$

As the lower limit of 1.8 is not reached, the focal depth becomes insufficient, often causing the pupil P of the subject to be out of focus and, hence, leading to inability to measure the pupillary diameter precisely.

It is even more preferable to satisfy condition (8):

$$Fno/P > 0.2 \quad (8)$$

Here P is the pixel pitch in μm of the imaging device 24. This condition is about focal depth, too. However, as the pixel pitch becomes small, the focal depth grows large, so it is desired to satisfy condition (5).

With the embodiment depicted in FIG. 15, it is noted that even when the semi-transmitting, second reflecting surface 26 is designed such that the alignment mark 22 provided on the back surface of the double-convex positive lens 25 is projected as a real image on the cornea of the eye E of the subject, there can again be no or little pupillary diameter variation due to a difference of the axial direction position of the eye E.

Figure 16:
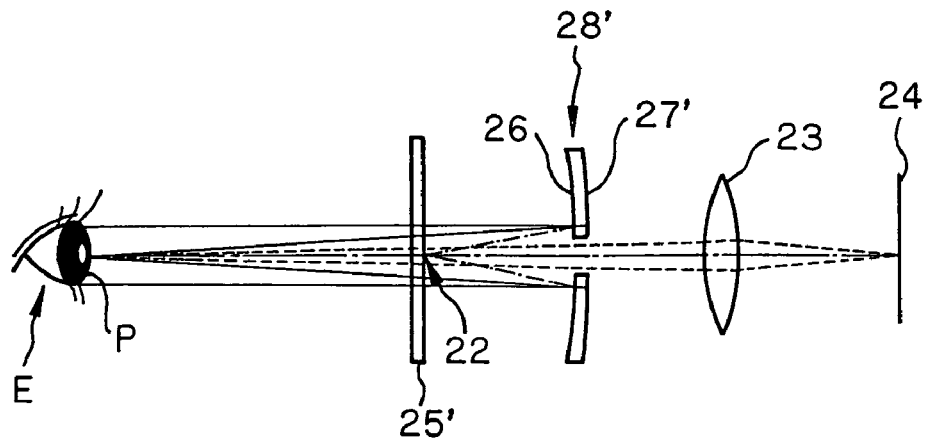
FIG. 16 is illustrative in section of an optical path for the optical positioning means according to the sixth embodiment of the present invention.

FIG. 16 is illustrative in section of an optical path taken by the optical positioning means according to the sixth embodiment that is a modification to the fifth one, wherein a reflecting surface 27' of a concave mirror is used in place of the reflecting surface 27 of the plane mirror of FIG. 15, and a plane-parallel plate 25' is used instead of the double-convex positive lens 25 having the alignment mark 22 on its back surface, with an alignment mark 22 provided on the back surface of that plane-parallel plate. That modification works the same way as does the fifth embodiment.

Figure 17A:
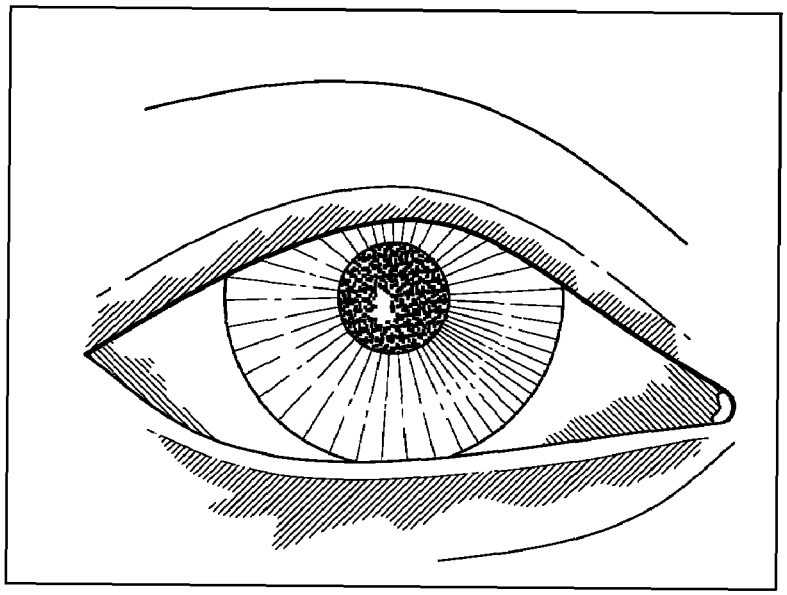
FIG. 17 is illustrative of what relations the subject's own image seen in the cases of FIGS. 11 to 16 has to an alignment mark image.
Figure 17B:
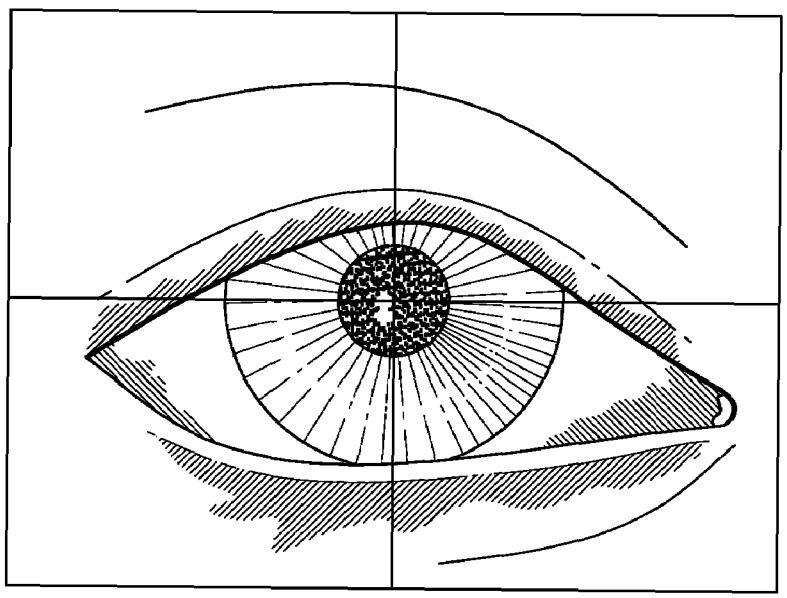

FIG. 17 is illustrative of, in the above embodiments of FIGS. 11 to 16, what relations the image of the subject's own pupil P observed by the subject herself or himself has to the image of the alignment mark. FIG. 17(a) is illustrative of what relations the image of the subject's own pupil P seen in the embodiment of FIGS. 11 to 14 has to the image of the alignment mark (crosshairs). With the diopter of the subject's own eye E in alignment with the image of the subject's own pupil P, the image of the alignment mark (crosshairs) becomes blurred, yet it is quite possible to align the image of the pupil P with the center of the alignment mark (crosshairs). FIG. 17(b) is illustrative of what relations the image of the subject's own pupil P seen in the embodiment of FIGS. 15 and 16 has to the image of the alignment mark (crosshairs). The image of the subject's own pupil P and the image of the alignment mark (crosshairs) are formed in much the same axial direction position; both images can be clearly seen, making the alignment of the image of the pupil P with the center of the alignment mark (crosshairs) easy.

Embodiments of the illumination system are now explained with reference to FIG. 12 showing the addition of the illumination system to the arrangement of the second embodiment. The same shall apply to other embodiments as well.

Figure 18:
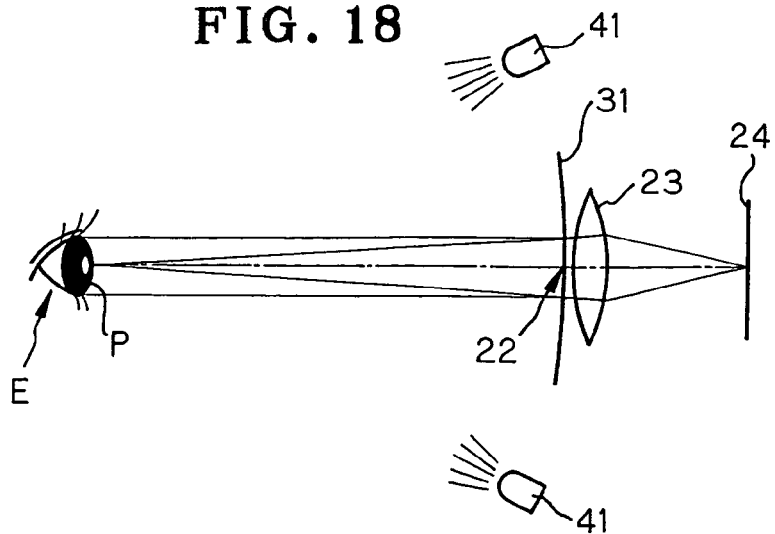
FIG. 18 is illustrative in section of one exemplary array of infrared light sources for taking a pupillary image.

FIG. 18 is illustrative of an embodiment wherein the eye E of a subject is irradiated with infrared radiation from a single or multiple infrared LEDs 41 located around a concave mirror 31 and off a taking optical axis to take an image of the pupil P with reflected scattered light. Note here that because it is relatively likely that the light from the infrared LED 41 may be reflected at the surface of the cornea of the eye E, it is sometimes impossible to take a clear image of the pupil P. Therefore, it is desired that although not illustrated, two sheet polarizers be located in front of the infrared LED 41 and before or after an image-formation optical system 23 in a mutually crossed Nicols state to eliminate that surface reflected light and thereby take a clear image of the pupil P.

Figure 19:
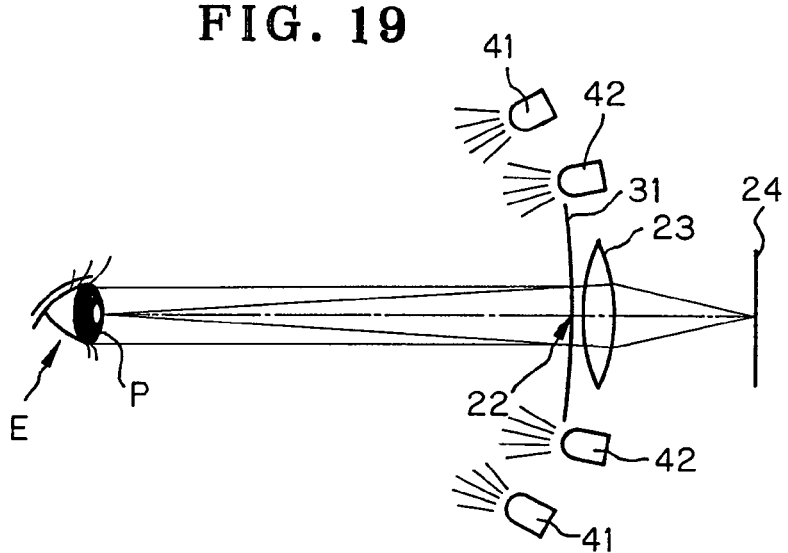
FIG. 19 is illustrative in section of one exemplary array of an infrared light source and a visible photo-stimulating light source for taking a pupillary image.

FIG. 19 is illustrative of an embodiment wherein, in the arrangement of FIG. 18, a single or multiple visible light sources 42 emitting visible stimulating light are located around a concave mirror 31 and off a taking optical axis to direct that light toward the pupil P and thereby examine pupillary light reflex.

Figure 20:
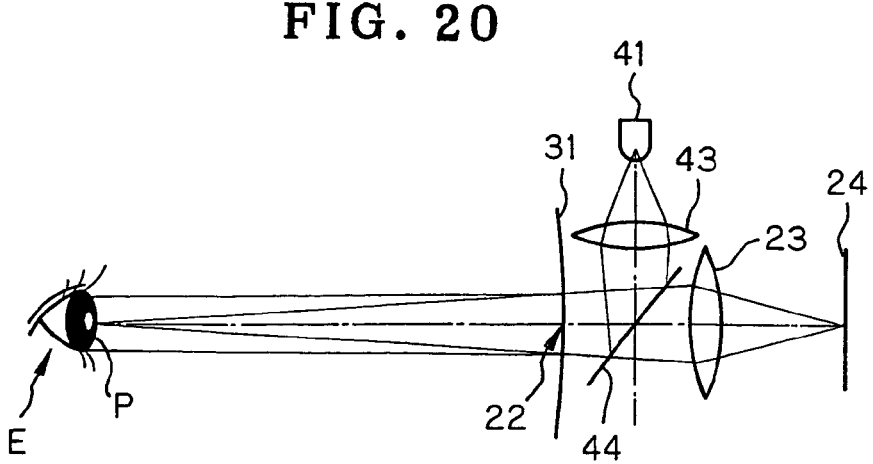
FIG. 20 is illustrative in section of one exemplary arrangement for illuminating the pupil with infrared illumination light coaxially with an image-formation optical system.

FIG. 20 is illustrative of an arrangement wherein a concave mirror 31 is built up of a half-silvered mirror or a dichromatic mirror that reflects visible light and transmits infrared light, and infrared illumination light is directed to the pupil P coaxially with an image-formation optical system 23. Light from an infrared LED 41 located off an optical axis is converted by a condensing lens 43 into converging light, and that converging light is coaxially reflected toward the pupil P by a half-silvered mirror 44 located between the concave mirror 31 and the image-formation optical system 23. This arrangement makes it possible to detect light reflected at the eyeground of the subject's eye E, and is much less vulnerable to noises such as reflection of infrared illumination light at the cornea (the first Purkinje image).

Figure 21:
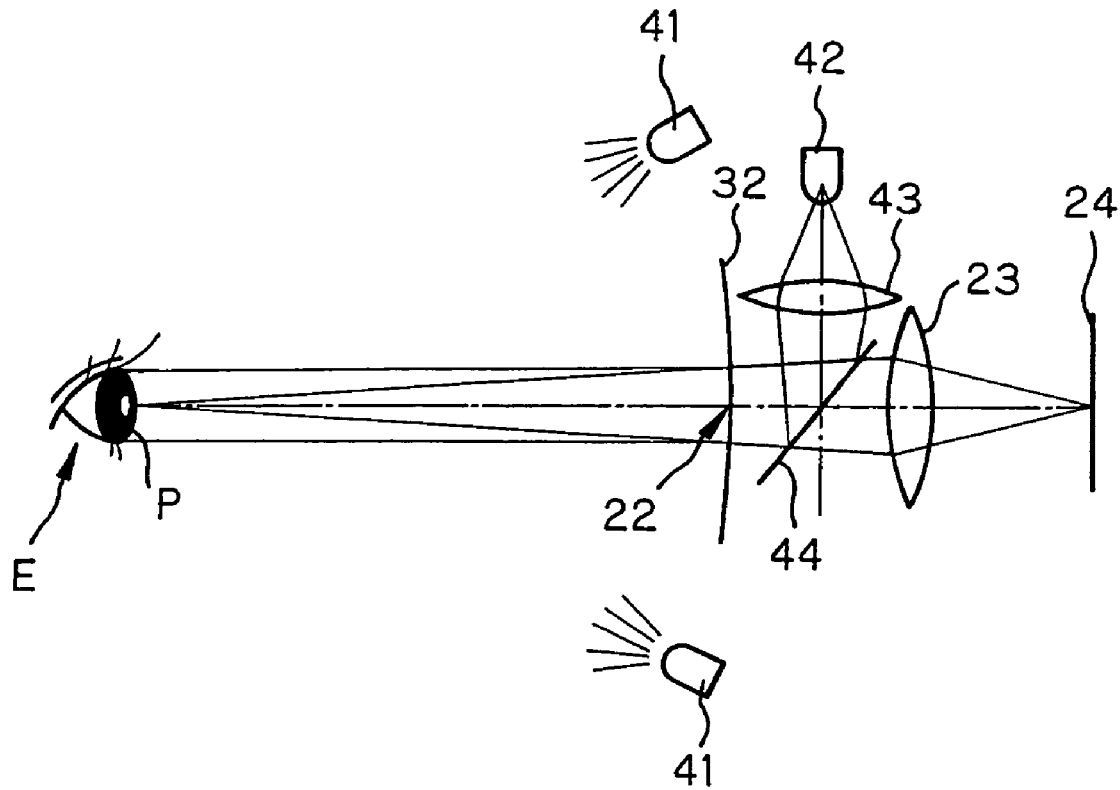
FIG. 21 is illustrative in section of an arrangement wherein a visible photo-stimulating light source is located coaxially with an image-formation optical system and off the axis for taking a pupillary image.

FIG. 21 is illustrative of an arrangement wherein a visible light source 42 emitting visible stimulating light is located at the position of the infrared LED 41 in FIG. 20, and a single or multiple infrared LEDs 41 that are illumination light sources for taking an image of the pupil P are located around a concave mirror 31 and off a taking optical system. Stimulating light from the visible light source or sources 42 is stopped down to a diameter of 1 mm or less at the position of the subject's pupil P so that it can reach down to the eyeground with the diameter of the pupil P yet without being shaded. Thus, it is possible to give an always constant stimulus to the pupil P irrespective of the pupillary diameter before stimulation.

Figure 22:
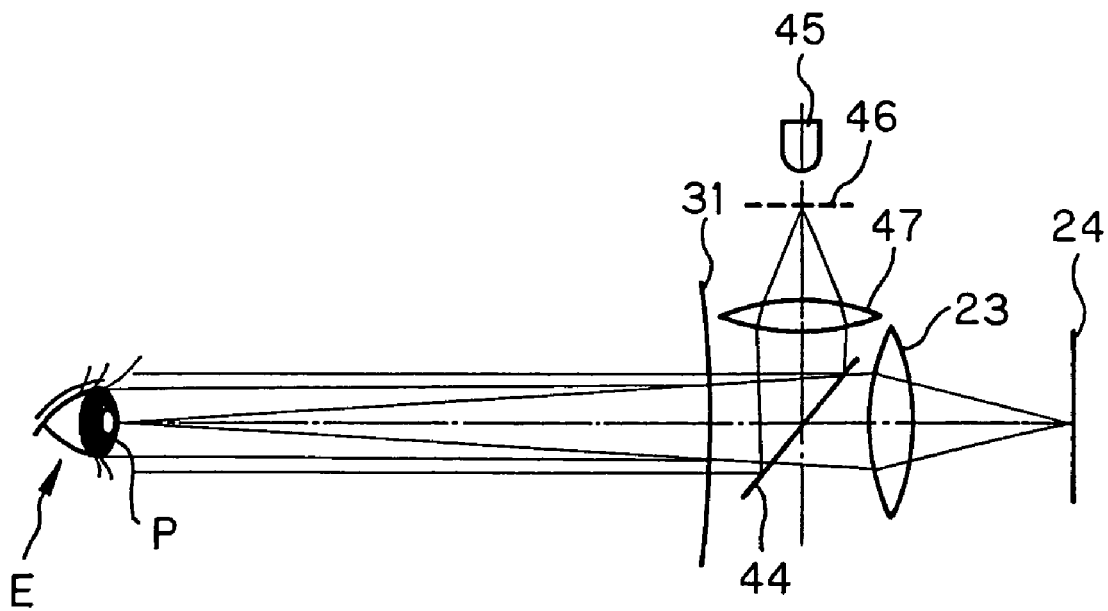
FIG. 22 is illustrative in section of an arrangement wherein an alignment mark illumination light source and an alignment mark are coaxially located off an optical axis.

FIG. 22 is illustrative of an arrangement wherein a concave mirror 31 is built up of a half-silvered mirror, a visible alignment mark illumination light source 45 is located off an optical axis and a circular slit-form alignment mark 46 located in front of the same, a projection lens 47 is located on the projection side of the alignment mark 46, and a half-silvered mirror 44 is located between the concave mirror 31 and an image-formation optical system 23, so that light projected by the projection lens 47 from the alignment mark 46 is coaxially reflected by that half-silvered mirror 44 toward the pupil P. A virtual image of the alignment mark 46 is presented from infinity to a position of 30 cm in front of the subject's eye E. As the subject aligns the position of the iris P of the image of the subject's own eye E with that virtual image of the alignment mark 46, the position in a direction orthogonal to the optical axis is fixed. And then, the physiological information acquisition and presentation kit 1 or the head of a subject M is moved back and forth to the position where both the image of the pupil P and the virtual image of the alignment mark 45 are clearly seen, whereby the position in the axial direction, too, can be unequivocally determined.

It is noted that when the physiological information acquisition and presentation kit 1 is used in the form of the embodiments of FIGS. 14 to 16 wherein the optical member is located on the viewing side of the plane mirror 21 or the concave mirror 31, the taking unit using the optical positioning means according to the embodiments of FIGS. 14 to 16, etc. is incorporated in another member separate from the compact mirror 12, for instance, a lid portion of the compact, not behind the compact mirror 12.

Figure 23:
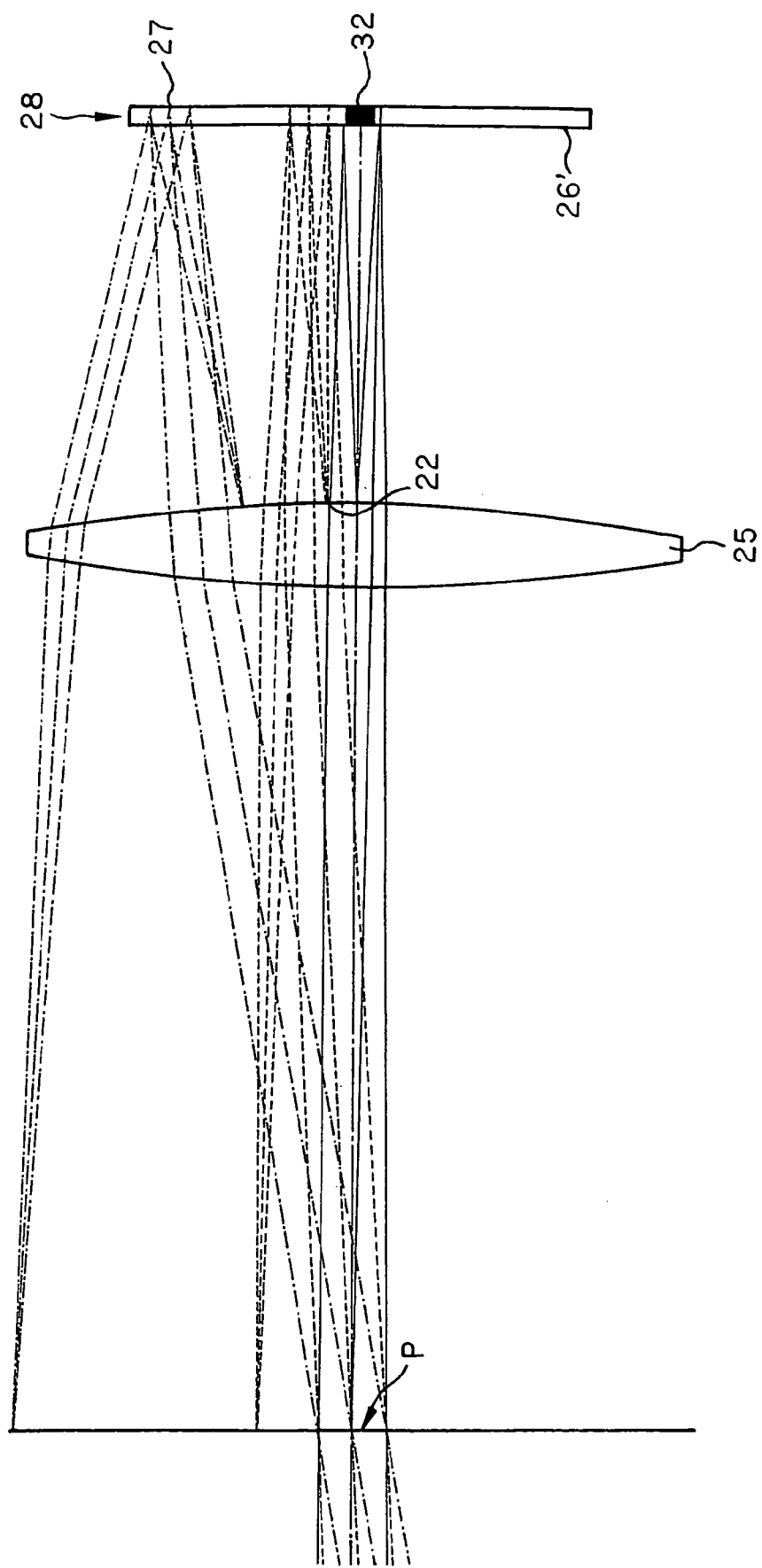
FIG. 23 is an optical path diagram indicative of one specific numerical example of a taking optical system using the optical positioning means of the present invention.

The present invention is now explained more specifically with one specific numerical example of the taking optical system using the inventive positioning means. FIG. 23 is an optical path view for that example, which corresponds to the embodiment wherein the alignment mark 22 of FIG. 15 is formed as a virtual image, and the concave mirror for the semi-transmitting, second reflecting surface 26 of FIG. 15 is built up of a semi-transmitting Fresnel reflecting mirror 26', as described just below. The first plane mirror 27 is built up of a plane mirror for making it possible for the subject to observe the subject's pupil P, and the concave Fresnel reflecting mirror 26' for the second reflecting surface has a semi-transmitting function of projecting the alignment mark 22 provided on the back surface of the double-convex positive lens 25 as a virtual image onto a 326.03 mm position in front of the subject's pupil P. Between the reflecting surfaces 26' and 27', a transparent medium having a refractive index of 1.5163 and an Abbe constant of 64.1 is located to build up a negative power back-surface mirror 28 whose front surface has a semi-transmitting function. Such arrangement ensures that the virtual image of the subject's pupil P is seen at the 326.03 mm position in front of the subject's eye E by way of the double-convex positive lens 25 and the negative power back-surface mirror 28. On the other hand, the alignment mark 22 provided on the back surface of the double-convex positive lens 25 is seen as a virtual image overlapping the image of the subject's pupil P at the 326.03 mm position in front of the subject's eye E by way of the semi-transmitting Fresnel concave mirror 26' and the double-convex positive lens 25.

Numerical data about that numerical example are given below. Data obtained by back ray tracing of the subject's pupil P are set out in Table 1, and data obtained by back ray tracing of the virtual image of the alignment mark 22 are set out in Table 2. In Tables 1 and 2, "Object Plane" refers to the images of the pupil P and the alignment mark 22 as virtual images at the 326.03 mm position in front of the subject's pupil P; "Surface No. 1" and "Image Plane" in Table 1 and "Surface No. 1" in Table 2 refer to the position of the pupil (iris) P; "Surface No. 2, 8" in Table 1 and "Surface NO. 2" in Table 2 refer to the surface of the double-convex positive lens 25 on the pupil P side; "Surface No. 3, 7 in Table 1 and "Surface No. 2" in Table 2 refer to the surface of the double-convex positive lens 25 on the image-formation optical system 23 side; "Surface No. 4, 6" in Table 1 refers to a Fresnel transmitting surface whose Fresnel reflecting mirror 26' functions as a transmitting surface; "Surface No. 4" in Table 2 refers to a Fresnel reflecting surface whose Fresnel reflecting mirror 26' functions as a reflecting surface; and "Surface No. 5" in Table 1 refers to the first reflecting surface 27.

TABLE 1

| Surface No. | Radius of Curvature | Surface Spacing | Refractive Index | Abbe Constant |
|---|---|---|---|---|
| Object Plane | ∞ (VI) | −326.03 | | |
| 1 | ∞ (Stop) | 50.00 | | |
| 2 | 102.80 | 5.00 | 1.5163 | 64.1 |
| 3 | −102.80 | 22.04 | | |
| 4 | −81.00 (FTS) | 1.00 | 1.5163 | 64.1 |
| 5 | ∞ (RF) | −1.00 | 1.5163 | 64.1 |
| 6 | −81.00 (FTS) | −22.4 | | |
| 7 | −102.80 | −5.0 | 1.5163 | 64.1 |
| 8 | 102.80 | −50.00 | | |
| Image Plane | ∞ (Iris) | 0.00 | | |

VI: virtual image
FTS: Fresnel transmitting surface
RF: reflecting surface

TABLE 2

| Surface No. | Radius of Curvature | Surface Spacing | Refractive Index | Abbe Constant |
|---|---|---|---|---|
| Object Plane | ∞ (VI) | −326.03 | | |
| 1 | ∞ (Stop) | 50.00 | | |
| 2 | 102.80 | 5.00 | 1.5163 | 64.1 |
| 3 | −102.80 | 22.04 | | |
| 4 | −81.00 (FFS) | −22.04 | | |
| Image Plane | −102.80 (Alignment Mark) | | | |

VI: virtual image
FFS: Fresnel reflecting surface

It is here noted that the focal length, f, of the pupil observation optical system in this example is $$f = -129.092$$

It is also noted that the focal length, f, and F-number, Fno, of the image-formation optical system 23, the pixel pitch, P, of the imaging device 24, and the spacing E between the entrance pupils of the first reflecting surface 27 and the imaging device 23 are f=12.0

Fno=2.0

P=4 μm

E=2 mm

EXAMPLE 3

Figure 24:
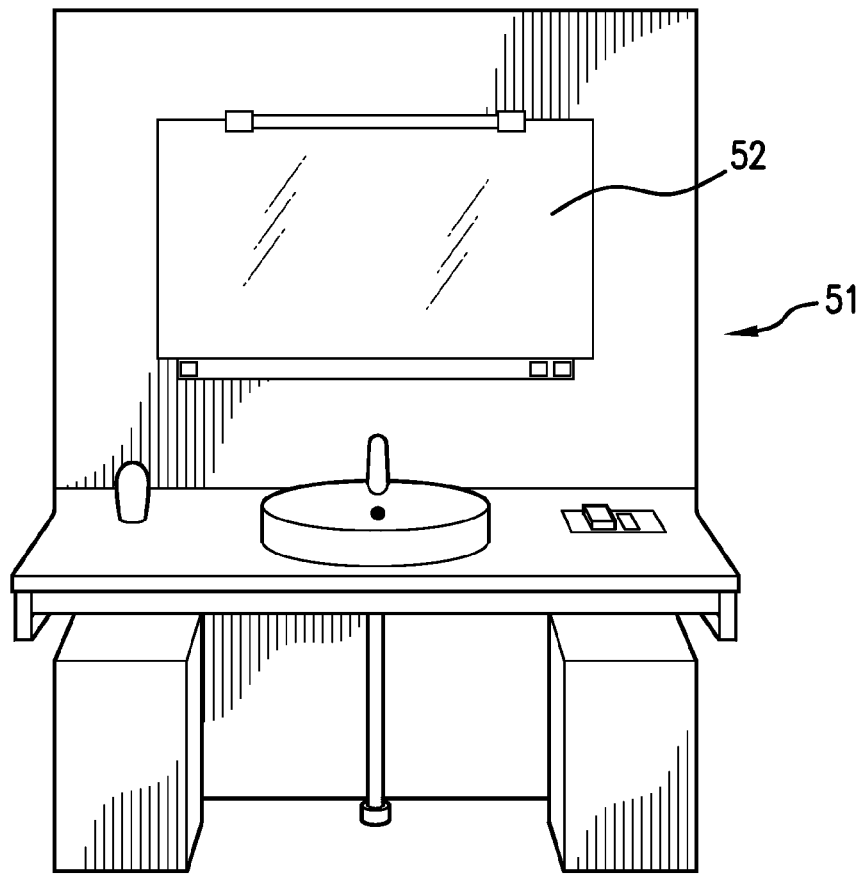
FIG. 24 is illustrative of the physiological information acquisition and presentation kit according to Example 3 of the present invention.
Figure 25:
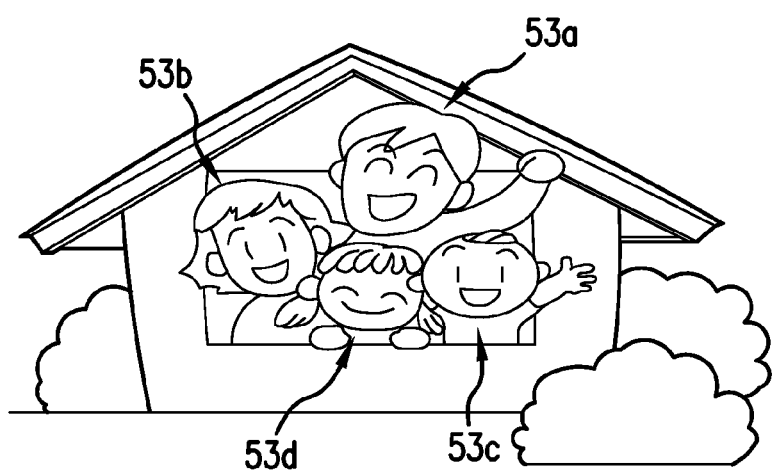
FIG. 25 is illustrative of buttons for identifying who is the subject in Example 3.

FIG. 24 is illustrative of a dressing table 51 whose mirror 52 is designed to function as the plane mirror 21 in the arrangement of FIG. 11. Behind that mirror 52, there is the taking optical system, etc. of the inventive physiological information acquisition and presentation kit 1 built in. While looking at her or his own face, the subject can measure her or his own pupillary diameter variations, etc.

In the example here, some family members could share one single measuring kit. Preferably in that case, each one individual should make a selection from exclusive buttons 53a to 53d assigned to her or him. It is also possible to identify who is the subject from the iris pattern taken.

EXAMPLE 4

Figure 26:
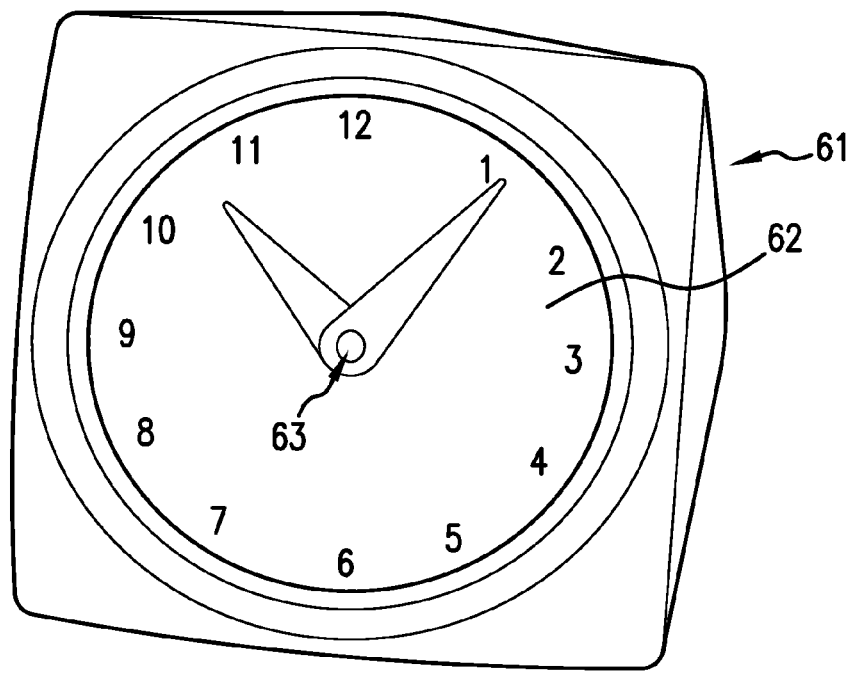
FIG. 26 is illustrative of the physiological information acquisition and presentation kit according to Example 4 of the present invention.

FIG. 26 is illustrative of an alarm clock 61 having a dial plate 62 made up of a reflecting surface, wherein the center 63 of the dial plate 62 is holed or formed of a reflecting surface. Then, the inventive physiological information acquisition and presentation kit 1 is mounted in that reflecting surface or behind the hole. In this way, the subject can measure her or his own pupillary diameter while looking at the clock.

EXAMPLE 5

Figure 27:
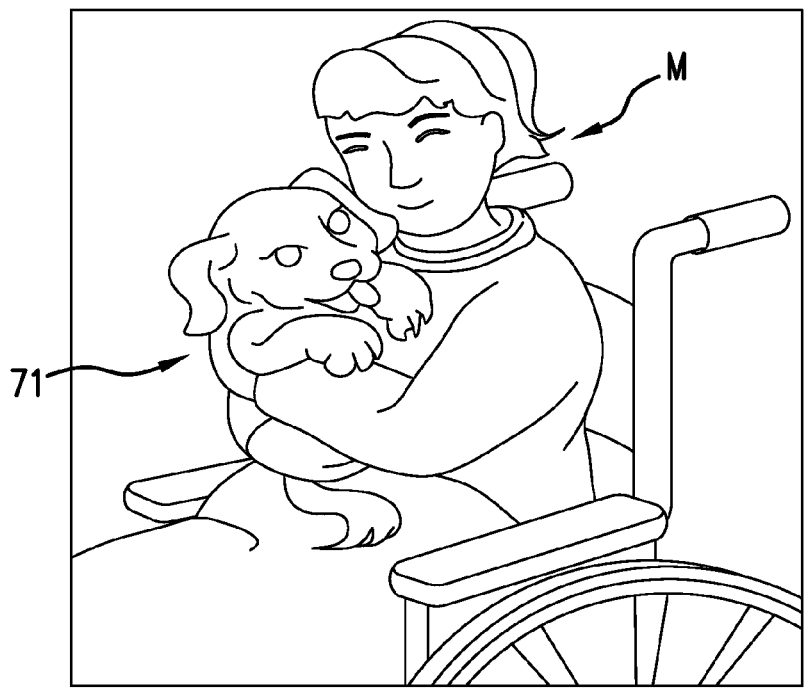
FIG. 27 is illustrative of the physiological information acquisition and presentation kit according to Example 5 of the present invention.

An example depicted in FIG. 27 is directed to a toy, specifically a dog robot 71, having the inventive physiological information acquisition and presentation kit 1 built in it. The robot 71 then comprises an imaging optical system adapted to take an image of the subject's eyeball on a portion corresponding to the head or the eye of the dog. It is then required for that imaging optical system to have a mechanism capable of searching out and track the eyeball of a subject M, wherein the eye of the subject M is searched out of a screen by means of template matching, and the trunk or the neck of the dog is moved in that direction to search out and track the eyeball of the subject M. In addition, the subject M could be under the impression that the dog robot peers at her or his own eye.

EXAMPLE 6

Figure 28:
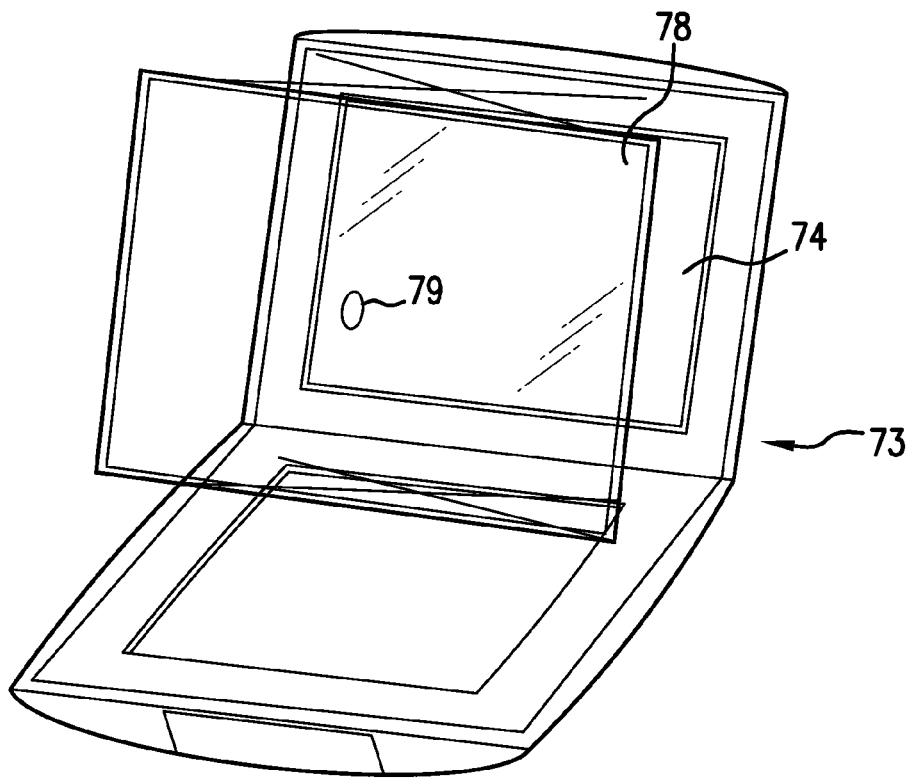
FIG. 28 is illustrative of the physiological information acquisition and presentation kit according to Example 6 of the present invention.
Figure 29A:
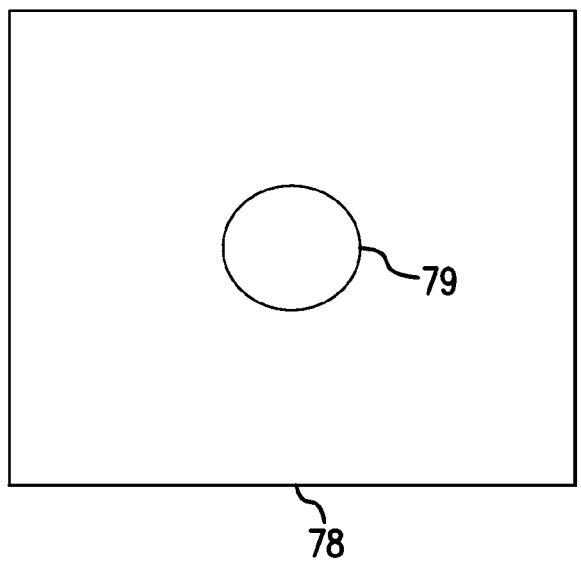
FIG. 29 is a rear and a sectional view of one example of the light guide sheet used in Example 6.
Figure 29B:
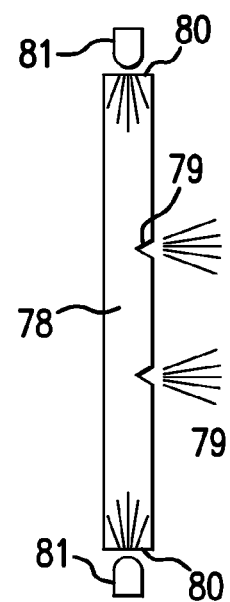

FIG. 28 is illustrative of a compact 73 in which a light guide plate 78 equivalent to the plane-parallel plate 25' in the arrangement of FIG. 16 is erectably or detachably mounted in front of, and some distance away from, its compact mirror 74. An alignment mark 79, on the one hand, is provided on the back surface of that light guide plate 78 in a displayable way, and the inventive physiological information acquisition and presentation kit 1, on the other hand, is incorporated behind the compact mirror 74. Thus, the subject can measure her or his own pupilary diameter while putting on makeup, etc. FIGS. 29(a) and 29(b) are a rear and a sectional view of one example of that light guide plate 78. As illustrated, a light source 81 for illuminating the alignment mark is located facing an end face 80 of the light guide plate 78, and illumination light from that light source 78 is admitted into the light guide plate 78 such that it travels through the light guide plate 78 while subjected to repetitive total reflections. The thus guided illumination light arrives at a groove line cut in as the alignment mark 79, where it is scattered at the position of that alignment mark 79 to display the alignment mark 79 brightly.

While the inventive physiological information acquisition and presentation kit and the inventive pupillary diameter measurement kit have been described with reference to some examples, it should be appreciated that the invention is never limited to such examples and many modifications are possible.

What I claim is:

1. A biological information acquisition and presentation kit, characterized by comprising a positioning means capable of being positioned on an axial focus position of a taking optical system that allows a subject to take an image of a subject's eyeball by herself or himself, an imaging means adapted to take an image of the subject's eyeball, a measurement means adapted to measure a physiological index from the image taken of the eyeball, a conversion means adapted to convert the physiological index detected by said measurement means into an emotional index, and a recording means adapted to record said physiological index or said emotional index, and further comprising a presentation means adapted to present comparative information with a recorded past emotional index.

2. The biological information acquisition and presentation kit according to claim 1, characterized in that said positioning means comprises an optical system having positive power, which is adapted to enlarge a subject's pupil, permitting the subject to observe an enlarged subject's pupil.

3. The biological information acquisition and presentation kit according to claim 1, characterized in that said physiological index is a rotary motion of the eyeball or nictitation.

4. The biological information acquisition and presentation kit according to claim 1, characterized in that said physiological index is a pupillary diameter.

5. The biological information acquisition and presentation kit according to claim 1, characterized in that said imaging means comprises an infrared illumination means, and imaging is implemented by infrared radiation.

6. The biological information acquisition and presentation kit according to claim 1, characterized in that said imaging means comprises a photo-stimulating means adapted to bring on a visible photo-stimulus.

7. The biological information acquisition and presentation kit according to claim 1, characterized by further comprising an identifying function capable of specifying who is the subject.

8. The biological information acquisition and presentation kit according to claim 1, characterized in that said emotional index is a one-dimensional variable indicative of antagonistic activation of a sympathetic nerve and a parasympathetic nerve of the autonomic nervous system.

9. The biological information acquisition and presentation kit according to claim 1, characterized in that said emotional index is a two-dimensional variable indicative of antagonistic activation of a sympathetic nerve and a parasympathetic nerve of the autonomic nervous system, respectively.

10. The biological information acquisition and presentation kit according to claim 1, characterized by further comprising a clock adapted to record measuring time along with said physiological index or said emotional index.

11. The biological information acquisition and presentation kit according to claim 1, characterized by further having a day, week, month or year-base variation analysis mode capable of checking up periodicity of said physiological index or said emotional index.

12. The biological information acquisition and presentation kit according to claim 1, characterized in that said measurement means uses FFT or wavelet transformation.

13. The biological information acquisition and presentation kit according to claim 1, characterized by being attached to a compact.

14. The biological information acquisition and presentation kit according to claim 1, characterized by being attached to a dressing table.

15. The biological information acquisition and presentation kit according to claim 1, characterized by being of a cellular phone type.

16. A biological information acquisition and presentation kit according to claim 1, characterized by being of a toy type.

17. A biological information acquisition and presentation kit, characterized by comprising a search and track means adapted to search out and track a subject's eyeball, an imaging means adapted to take an image of the subject's eyeball, a measurement means adapted to measure a physiological index from the image taken of the eyeball, a conversion means adapted to convert the physiological index detected by said measurement means into an emotional index, and a recording means adapted to record said physiological index or said emotional index, and further comprising a presentation means adapted to present comparative information with a recorded past emotional index.

18. A pupillary diameter measurement kit that allows a subject to measure a subject's own pupillary diameter through a subject's own operation alone, characterized by comprising a reflecting surface having at least a reflection function of enabling the subject to observe by herself or himself an image of the subject's own pupil, an alignment mark that is located on said reflecting surface and adapted to align the subject's pupil, an infrared imaging device located in opposition to the subject's pupil with said reflecting surface interposed therebetween, an infrared illumination means adapted to illuminate the subject's pupil, a projection optical system adapted to project an image of the subject's pupil onto an imaging plane of said infrared imaging device, and an analysis means adapted to compute and analyze pupillary size on the basis of pupillary image information sent out of said infrared imaging device, wherein the subject moves by herself or himself the pupil position to align the pupil image on said reflecting surface with the alignment mark.

19. The pupillary diameter measurement kit according to claim 18, characterized by further comprising an optical system having positive power, which has a function of projecting the subject's pupil as an enlarged virtual image in front of the subject's pupil.

20. The pupillary diameter measurement kit according to claim 19, characterized in that said optical system having positive power comprises a positive lens or a positive Fresnel lens.

21. The pupillary diameter measurement kit according to claim 19, characterized in that said optical system having positive power comprises a concave mirror or a Fresnel concave mirror.

22. The pupillary diameter measurement kit according to claim 18, characterized in that said reflecting surface having a reflecting function is a semi-transmitting mirror.

23. The pupillary diameter measurement kit according to claim 18, characterized in that said reflecting surface having a reflecting function is a holed mirror.

24. The pupillary diameter measurement kit according to claim 18, characterized in that said reflecting surface having a reflecting function is a plane mirror.

25. The pupillary diameter measurement kit according to claim 18, characterized in that said reflecting surface having a reflecting function is a concave mirror.

26. The pupillary diameter measurement kit according to claim 18, characterized in that said infrared illumination means comprises a sheet polarizer adapted to turn illumination light into linearly polarized light, and said projection optical system is provided with another sheet polarizer that transmits linearly polarized light in a direction orthogonal to the first-mentioned sheet polarizer.

27. The pupillary diameter measurement kit according to claim 18, characterized by further comprising a surface having a second reflecting function of projecting the alignment mark in front of the subject's pupil.

* * * * *